United States Patent
Surnilla et al.

(10) Patent No.: US 9,709,482 B2
(45) Date of Patent: Jul. 18, 2017

(54) METHODS AND SYSTEMS FOR HUMIDITY DETERMINATION VIA AN OXYGEN SENSOR

(71) Applicant: Ford Global Technologies, LLC, Dearborn, MI (US)

(72) Inventors: Gopichandra Surnilla, West Bloomfield, MI (US); Daniel A. Makled, Dearborn, MI (US); Richard E. Soltis, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 164 days.

(21) Appl. No.: 14/626,308

(22) Filed: Feb. 19, 2015

(65) Prior Publication Data

US 2016/0245198 A1    Aug. 25, 2016

(51) Int. Cl.
*F02D 41/14* (2006.01)
*G01N 7/00* (2006.01)
(Continued)

(52) U.S. Cl.
CPC .......... *G01N 19/10* (2013.01); *F02D 41/144* (2013.01); *F02D 41/1454* (2013.01); *G01M 15/104* (2013.01); *G01N 27/4074* (2013.01); *G01N 27/419* (2013.01); *F02D 41/0065* (2013.01); *F02D 41/123* (2013.01); *F02D 41/1456* (2013.01); *F02D 2041/1472* (2013.01); *F02D 2200/0418* (2013.01)

(58) Field of Classification Search
CPC ............. F02D 41/1438; F02D 41/0007; F02D 41/005; F02D 41/123; F02D 41/0055; F02D 41/1454; F02D 41/1444; F02D 41/0005; F02D 2041/1472; F02D 2200/0418; F02D 13/0215; F02D 13/0203; G01N 19/10; G01M 15/10; G01M 15/104; G01M 15/102; F01N 11/00; F01N 2560/02; F01N 2560/025; F01N 2560/028
USPC ............................ 123/703; 70/29.01, 114.73
See application file for complete search history.

(56) References Cited

U.S. PATENT DOCUMENTS

| | | | | |
|---|---|---|---|---|
| 5,261,271 A | * | 11/1993 | Bihn | ................... G01M 15/106 |
| | | | | 73/114.76 |
| 5,287,283 A | * | 2/1994 | Musa | ................... G01M 15/09 |
| | | | | 123/690 |

(Continued)

OTHER PUBLICATIONS

Surnilla, G. et al., "Methods and Systems for Operating a Variable Voltage Oxygen Sensor," U.S. Appl. No. 14/517,601, filed Oct. 14, 2014, 42 pages.

(Continued)

*Primary Examiner* — Lindsay Low
*Assistant Examiner* — George Jin
(74) *Attorney, Agent, or Firm* — Julia Voutyras; McCoy Russell LLP

(57) ABSTRACT

Methods are provided for determining ambient humidity based on outputs from an intake air or exhaust gas sensor. In one example, an oxygen sensor may be operated as a variable voltage sensor, between a lower first voltage and a higher second voltage, to determine a dry air oxygen reading. Ambient humidity may then be determined based on the dry air oxygen reading and a third output of the oxygen sensor when operated at the lower first voltage and not in variable voltage mode.

19 Claims, 5 Drawing Sheets

(51) Int. Cl.
    *G01N 19/10*     (2006.01)
    *G01M 15/10*     (2006.01)
    *G01N 27/407*     (2006.01)
    *G01N 27/419*     (2006.01)
    *F02D 41/00*     (2006.01)
    *F02D 41/12*     (2006.01)

(56) References Cited

U.S. PATENT DOCUMENTS

| | | | |
|---|---|---|---|
| 6,016,796 | A | 1/2000 | Dalton |
| 8,056,393 | B2 * | 11/2011 | Kawase ............. G01N 27/4065 73/114.72 |
| 8,495,996 | B2 | 7/2013 | Soltis et al. |
| 8,522,760 | B2 | 9/2013 | Soltis |
| 8,603,310 | B2 | 12/2013 | Ishida et al. |
| 8,731,806 | B2 | 5/2014 | Soltis et al. |
| 8,857,155 | B2 | 10/2014 | Surnilla et al. |
| 9,017,217 | B2 | 4/2015 | Norman et al. |
| 2003/0089164 | A1 * | 5/2003 | Bonadies ............ F02D 41/1441 73/114.39 |
| 2004/0200271 | A1 * | 10/2004 | van Nieuwstadt . B01D 46/0036 73/114.78 |
| 2007/0045112 | A1 * | 3/2007 | Tashiro ................ F02D 41/123 204/401 |
| 2007/0068159 | A1 * | 3/2007 | Ueno ...................... F02D 23/00 60/605.2 |
| 2008/0262703 | A1 * | 10/2008 | Kawase ................ F02D 41/123 701/107 |
| 2014/0156172 | A1 | 6/2014 | Surnilla et al. |
| 2014/0202437 | A1 | 7/2014 | Surnilla et al. |
| 2014/0238368 | A1 | 8/2014 | Jammoussi et al. |
| 2014/0345584 | A1 | 11/2014 | Jammoussi et al. |
| 2015/0101328 | A1 | 4/2015 | Surnilla et al. |
| 2015/0121864 | A1 | 5/2015 | Surnilla et al. |
| 2016/0245204 | A1 * | 8/2016 | Makled ............... F02D 41/0295 |

OTHER PUBLICATIONS

Surnilla, G. et al., "Methods and Systems for Fuel Ethanol Content Determination via an Oxygen Sensor," U.S. Appl. No. 14/151,574, filed Jan. 9, 2014, 31 pages.

Surnilla, G. et al., "Methods and Systems for Fuel Ethanol Content Determination via an Oxygen Sensor," U.S. Appl. No. 14/297,301, filed Jun. 5, 2014, 35 pages.

Demarco, J. et al., "Engine Speed Control Via Alternator Load Shedding," U.S. Appl. No. 14/614,881, filed Feb. 5, 2015, 50 pages.

MacNeille, P. et al., "System and Method for Estimating Ambient Humidity," U.S. Appl. No. 14/286,631, filed May 23, 2014, 50 pages.

Vigild, C. et al., "Methods and Systems for Fuel Canister Purge Flow Estimation with an Intake Oxygen Sensor," U.S. Appl. No. 14/155,261, filed Jan. 14, 2014, 51 pages.

Makled, D. et al., "Methods and Systems for Estimating Air-Fuel Ratio with a Variable Voltage Oxygen Sensor," U.S. Appl. No. 14/626,542, filed Feb. 19, 2015, 47 pages.

Makled, D. et al., "Ambient Humidity Detection Transmission Shifts," U.S. Appl. No. 14/626,193, filed Feb. 19, 2015, 43 pages.

Makled, D. et al., "Methods and System for Fuel Ethanol Content Estimation and Engine Control," U.S. Appl. No. 14/626,623, filed Feb. 19, 2015, 68 pages.

* cited by examiner

METHODS AND SYSTEMS FOR HUMIDITY DETERMINATION VIA AN OXYGEN SENSOR

TECHNICAL FIELD

The present application relates generally to estimating ambient humidity with an oxygen sensor of an internal combustion engine.

BACKGROUND AND SUMMARY

During engine non-fueling conditions in which at least one intake valve and one exhaust valve are operating, such as deceleration fuel shut off (DFSO), ambient air may flow through engine cylinders and into the exhaust system. In some examples, an exhaust gas sensor may be utilized to determine ambient humidity during the engine non-fueling conditions. It may take a long time for the exhaust flow to be devoid of hydrocarbons during the engine non-fueling conditions, however, and, as such, an accurate indication of ambient humidity may be delayed. In one example, as shown in US 2014/0202135, an indication of ambient humidity may be determined based on a change in pumping current output by the oxygen sensor while modulating a reference voltage of the oxygen sensor between a lower first voltage (e.g., base voltage) and a higher second voltage. In this way, the oxygen sensor may be a variable voltage oxygen sensor capable of operating in a variable voltage mode.

However, the inventors have recognized that operating the oxygen sensor in the variable voltage mode may reduce the durability of the oxygen sensor. Specifically, operating the oxygen sensor at the higher second voltage may degrade the sensor, thereby reducing the longevity of the oxygen sensor. Operating the oxygen sensor in the variable voltage mode more frequently may increase a rate of degradation of the oxygen sensor.

In one example, the above issues may be addressed by a method for: applying to an oxygen sensor a lower first reference voltage to generate a first output and a higher second reference voltage to generate a second output during a first condition; applying the first reference voltage to the oxygen sensor to generate a third output during a second condition; and adjusting engine operation based on ambient humidity estimated based on the first, second, and third output. In this way, the oxygen sensor may only be operated in variable voltage mode during the first condition and oxygen sensor durability may be increased.

In one example, during selected conditions, the oxygen sensor is operated to determine an oxygen sensor reading corrected for dry air conditions. For example, during conditions when purge and crankcase ventilation gases are not ingested in an engine intake manifold, the reference voltage of an intake oxygen sensor may be modulated. Alternatively, in embodiments where the oxygen sensor is an exhaust oxygen sensor, the selected conditions may include engine non-fueling conditions, such as a deceleration fuel shut-off (DFSO) event. Specifically, the reference voltage of the oxygen sensor may be raised from a first, lower voltage where the output (e.g., pumping current) is representative of an oxygen reading in humid conditions, to a second, higher voltage where the output (e.g., pumping current) is representative of an increase in oxygen due to the full dissociation of humidity. A dry air pumping current may then be determined based on a ratio between the first output and the second output, the dry air pumping current indicative of an oxygen reading in dry air. The dry air oxygen reading (the ratio between the first and second output) may only be determined and updated periodically, such as following each engine start or after a duration of engine operation. Then, during engine operation when the selected conditions are met, the oxygen sensor may be operated at the first, lower voltage (and not the second, higher voltage). Ambient humidity may then be determined based on the previously determined dry air oxygen reading and the output of the oxygen sensor when operating only at the first, lower voltage. As such, multiple ambient humidity estimates may be taken while not operating the oxygen sensor in the variable voltage mode. A controller may then adjust engine operation based on the multiple ambient humidity estimates. By determining humidity based on a first oxygen sensor output at the lower, first voltage and comparing it to a dry air oxygen reading that is determined less frequently than the first oxygen sensor output, an amount of time in which the oxygen sensor operates in variable voltage mode may be reduced. As a result, degradation of the oxygen sensor may decrease while longevity of the sensor may increase.

It will be understood that the summary above is provided to introduce in simplified form a selection of concepts that are further described in the detailed description, which follows. It is not meant to identify key or essential features of the claimed subject matter, the scope of which is defined by the claims that follow the detailed description. Further, the claimed subject matter is not limited to implementations that solve any disadvantages noted above or in any part of this disclosure.

DETAILED DESCRIPTION

Figure 1:
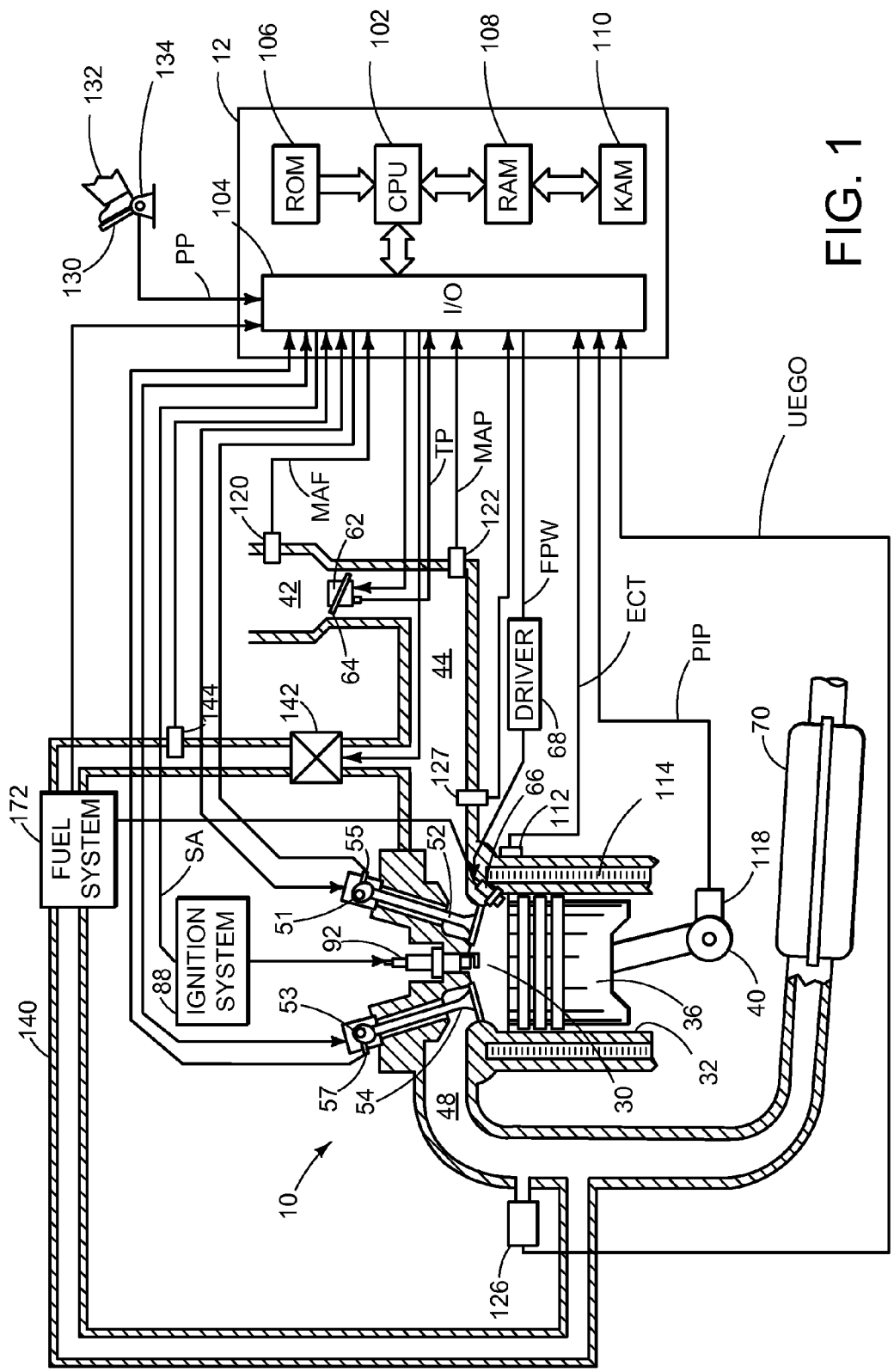
FIG. 1 shows a schematic diagram of an engine including an exhaust gas oxygen sensor and an intake gas oxygen sensor.
Figure 2:
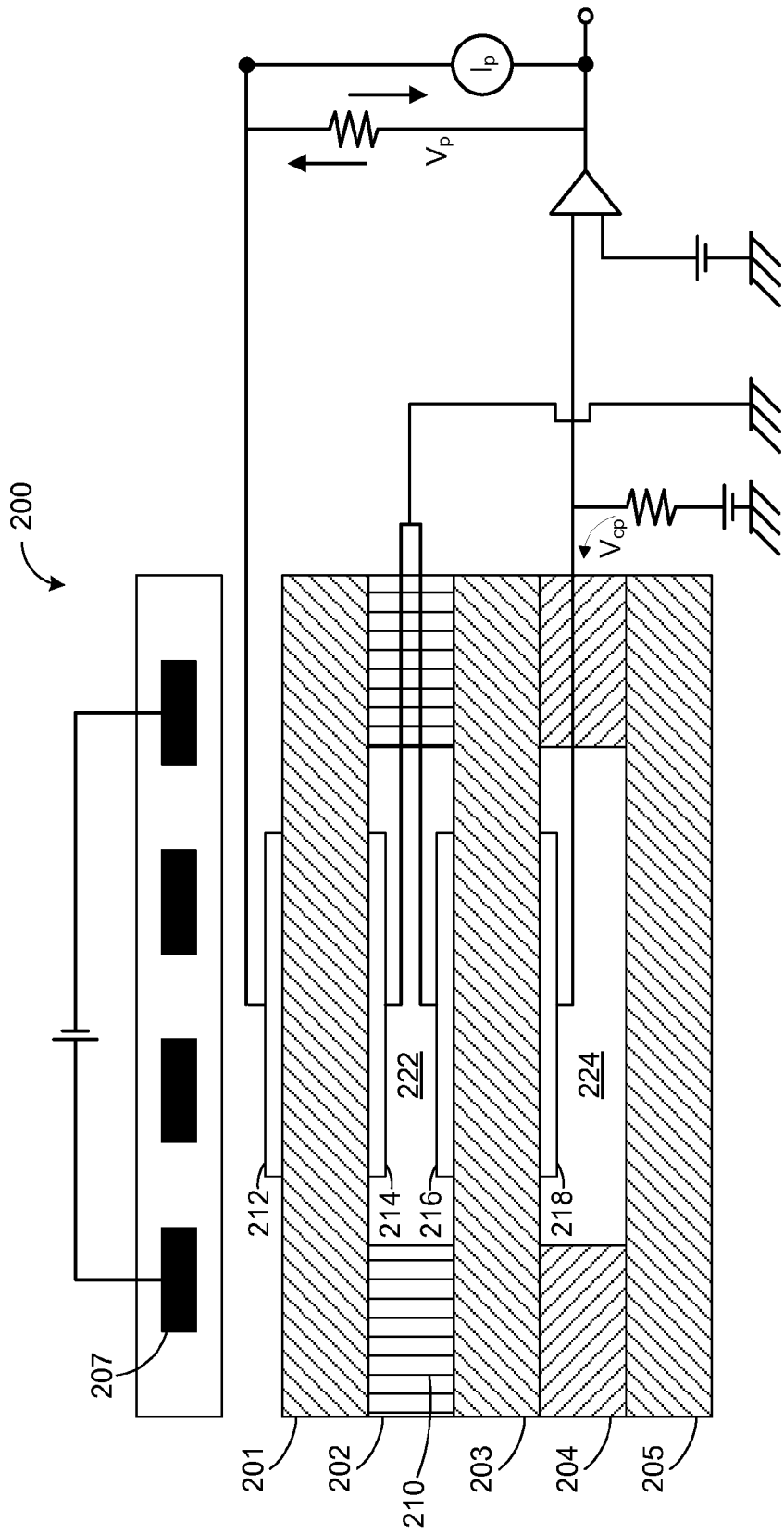
FIG. 2 shows a schematic diagram of an example oxygen sensor.
Figure 3:
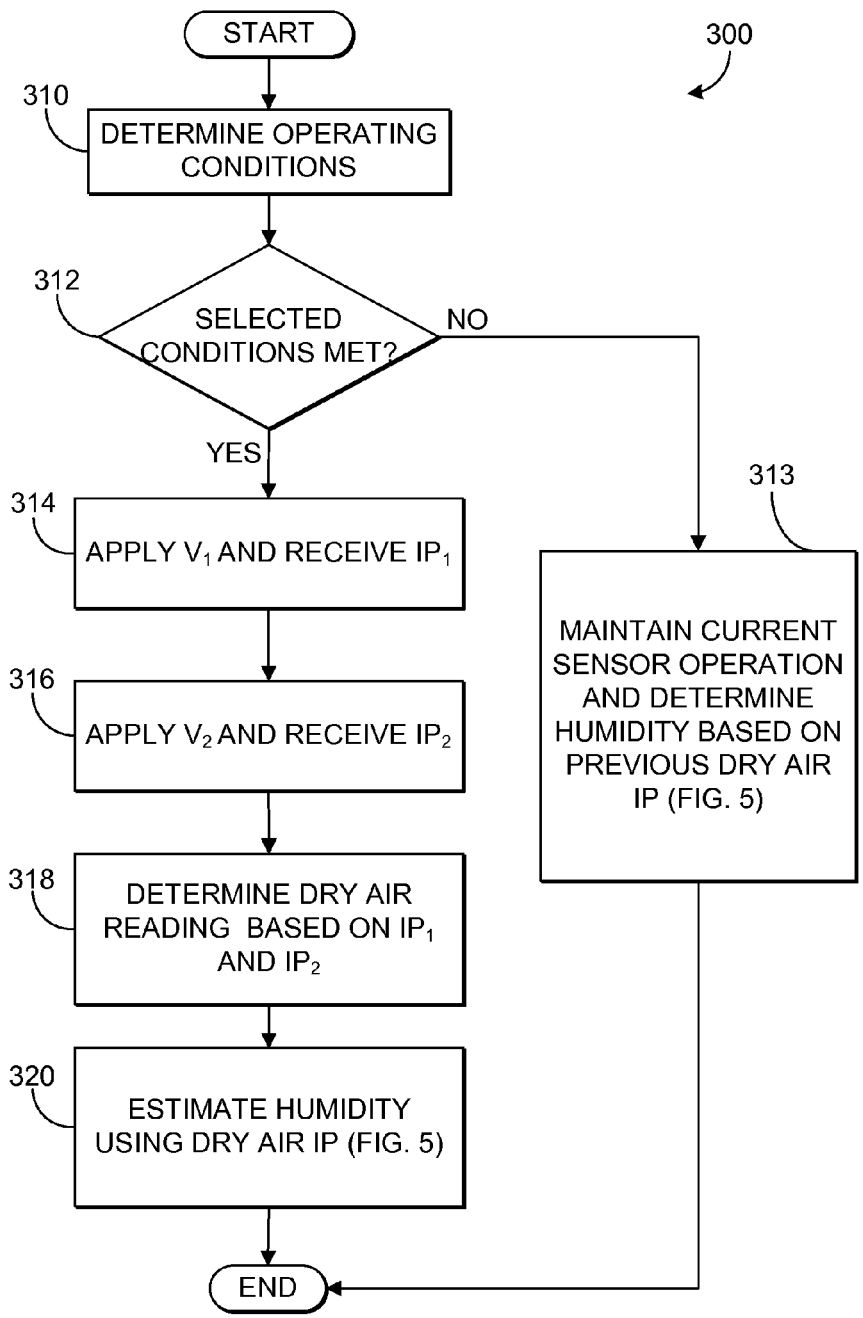
FIG. 3 shows a flow chart illustrating a routine for estimating a dry air pumping current with an oxygen sensor.
Figure 4:
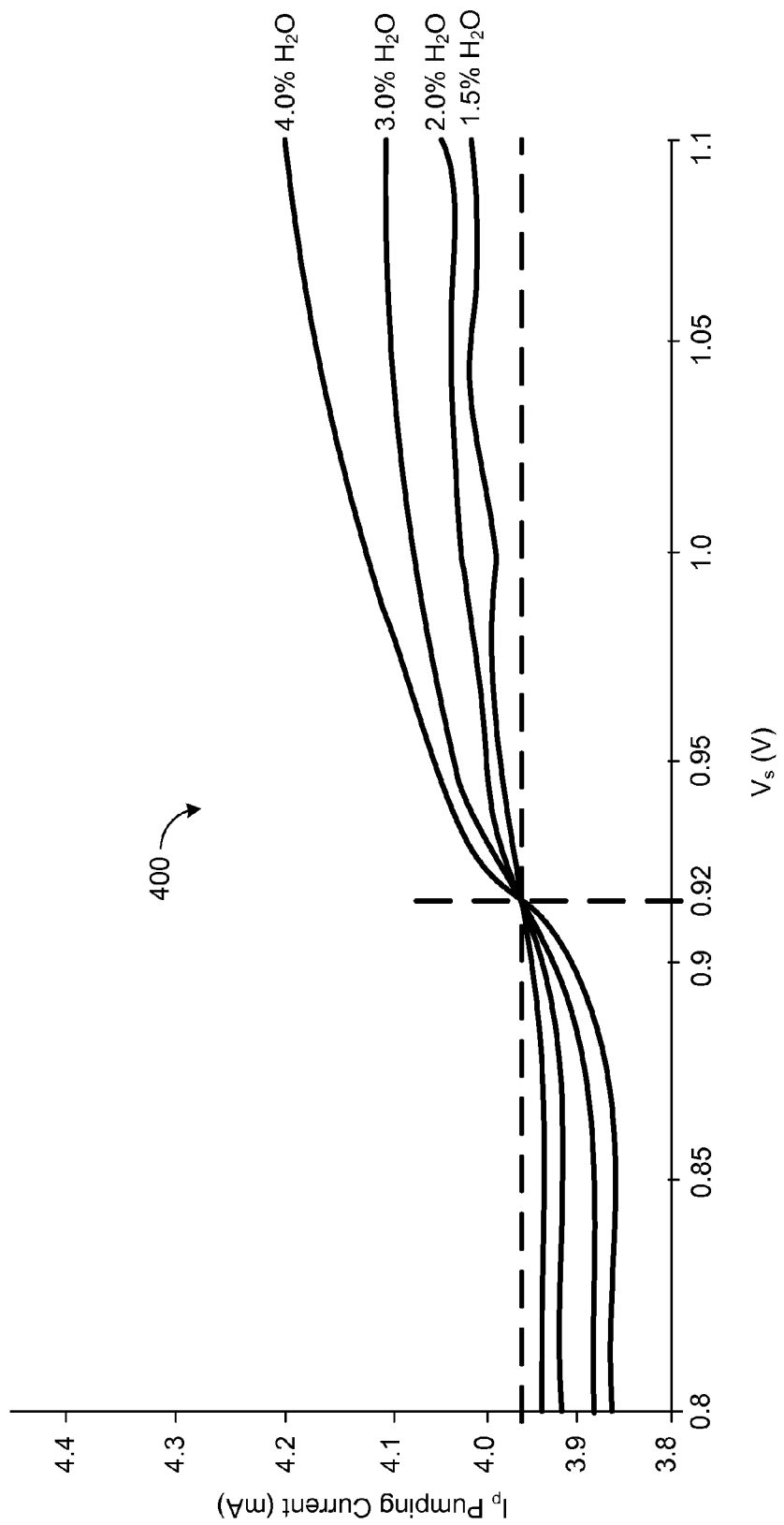
FIG. 4 shows a graph depicting oxygen sensor output under various humidity conditions with respect to applied voltage.

The following description relates to a method for determining ambient humidity based on outputs from an intake air or exhaust gas sensor, such as an oxygen sensor as shown in FIGS. 1-2. For example, as shown in FIG. 3, the sensor may be operated a first, lower voltage to obtain a first output which indicates a humid air oxygen reading. The sensor may then be operated at a second, higher voltage to obtain a second output which indicates a humid air oxygen reading wherein all the humidity in the air has dissociated at the oxygen sensor. A middle voltage between the first, lower voltage and the second, higher voltage may produce an oxygen sensor output indicative of a dry air oxygen reading wherein partial dissociation of the humidity occurs, as illustrated in FIG. 4. A dry air oxygen reading may then be estimated by a ratio between the first output and the second output. In this way, the dry air oxygen reading may be determined by operating the oxygen sensor in a variable voltage (VVs) mode. Subsequently, a third output of the oxygen sensor may be generated when operating the oxygen sensor at the first, lower voltage and not in the VVs mode. As shown in a method presented in FIG. 5, an estimate of ambient humidity may then be determined based on a difference between the dry air oxygen reading and the third output. Engine operation may then be adjusted based on the estimated ambient humidity. The dry air oxygen reading may be determined (and updated) periodically (e.g., at each engine start or after a duration of engine operation). The rest of the time, the oxygen sensor may not be operated in VVs mode and humidity may be determined by generating the third output while operating the oxygen sensor at the first, lower voltage and comparing the third output to the previously determined dry air oxygen reading. In this way, a more accurate estimate of ambient humidity may be determined for engine control while reducing degradation of the oxygen sensor due to operating in the VVs mode.

Referring now to FIG. 1, a schematic diagram showing one cylinder of a multi-cylinder engine 10, which may be included in a propulsion system of an automobile, is illustrated. The engine 10 may be controlled at least partially by a control system including a controller 12 and by input from a vehicle operator 132 via an input device 130. In this example, the input device 130 includes an accelerator pedal and a pedal position sensor 134 for generating a proportional pedal position signal PP. A combustion chamber (i.e., cylinder) 30 of the engine 10 may include combustion chamber walls 32 with a piston 36 positioned therein. The piston 36 may be coupled to a crankshaft 40 so that reciprocating motion of the piston is translated into rotational motion of the crankshaft. The crankshaft 40 may be coupled to at least one drive wheel of a vehicle via an intermediate transmission system. Further, a starter motor may be coupled to the crankshaft 40 via a flywheel to enable a starting operation of the engine 10.

The combustion chamber 30 may receive intake air from an intake manifold 44 via an intake passage 42 and may exhaust combustion gases via an exhaust passage 48. The intake manifold 44 and exhaust passage 48 can selectively communicate with the combustion chamber 30 via respective intake valve 52 and exhaust valve 54. In some embodiments, the combustion chamber 30 may include two or more intake valves and/or two or more exhaust valves.

In this example, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by a controller 12 to vary valve operation. The position of the intake valve 52 and exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. The fuel injector 66 is shown coupled directly to the cylinder 30 for injecting fuel directly therein in proportion to the pulse width of signal FPW received from the controller 12 via an electronic driver 68. In this manner, the fuel injector 66 provides what is known as direct injection (hereafter also referred to as "DI") of fuel into the combustion cylinder 30.

It will be appreciated that in an alternate embodiment, the injector 66 may be a port injector providing fuel into the intake port upstream of the cylinder 30. It will also be appreciated that the cylinder 30 may receive fuel from a plurality of injectors, such as a plurality of port injectors, a plurality of direct injectors, or a combination thereof.

A fuel tank in a fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios therebetween, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day to day variations in tank refilling can thus result in frequently varying fuel composition of the fuel in the fuel system 172, thereby affecting the fuel composition and/or fuel quality delivered by the injector 66. The different fuel compositions injected by the injector 66 may herein be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased.

Continuing with FIG. 1, the intake passage 42 may include a throttle 62 having a throttle plate 64. In this particular example, the position of the throttle plate 64 may be varied by the controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by a throttle position signal TP. The intake passage 42 may include a mass air flow sensor 120 and a manifold air pressure sensor 122 for providing respective signals MAF and MAP to controller 12.

An ignition system 88 can provide an ignition spark to the combustion chamber 30 via a spark plug 92 in response to a spark advance signal SA from the controller 12, under select operating modes. Though spark ignition components are shown, in some embodiments, the combustion chamber 30 or one or more other combustion chambers of the engine 10 may be operated in a compression ignition mode, with or without an ignition spark.

An exhaust gas sensor 126 is shown coupled to the exhaust passage 48 upstream of an emission control device 70. The exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. The emission control device 70 is shown arranged along the exhaust passage 48 downstream of the exhaust gas sensor 126. The device 70 may be a three way catalyst (TWC), $NO_x$ trap, various other emission control devices, or combinations thereof. In some embodiments, during operation of engine 10, emission control device 70 may be periodically reset by operating at least one cylinder of the engine within a particular air/fuel ratio.

As shown in the example of FIG. 1, the system further includes an intake air sensor (e.g., intake oxygen sensor) 127 coupled to the intake passage 44. The intake air sensor 127 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor.

Further, in the disclosed embodiments, an exhaust gas recirculation (EGR) system may route a desired portion of exhaust gas from the exhaust passage 48 to the intake passage 44 via an EGR passage 140. The amount of EGR provided to the intake passage 44 may be varied by the controller 12 via an EGR valve 142. Further, an EGR sensor 144 may be arranged within the EGR passage 140 and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

The controller 12 is shown in FIG. 1 as a microcomputer, including a microprocessor unit 102, input/output ports 104, an electronic storage medium for executable programs and calibration values shown as read only memory chip 106 in this particular example, random access memory 108, keep alive memory 110, and a data bus. The controller 12 may receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; and absolute manifold pressure signal, MAP, from the sensor 122. Engine speed signal, RPM, may be generated by the controller 12 from signal PIP.

The storage medium read-only memory 106 can be programmed with computer readable data representing instructions executable by the processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Next, FIG. 2 shows a schematic view of an example embodiment of an oxygen sensor 200 configured to measure a concentration of oxygen ($O_2$) in an intake airflow in an intake passage or an exhaust gas stream in an exhaust passage. The sensor 200 may operate as exhaust gas sensor 126 or intake air sensor 127 of FIG. 1, for example. The sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce exhaust gases into a first internal cavity 222 via diffusion. The diffusion path 210 may be configured to allow one or more components of intake air or exhaust gases, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition, e.g., an oxygen level present in the second internal cavity 224 is equal to that which the intake air or exhaust gas would have if the air-fuel ratio was stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture.

A pair of pumping electrodes 212 and 214 is disposed in communication with the internal cavity 222, and is configured to electrochemically pump a selected gas constituent (e.g., $O_2$) from internal cavity 222 through layer 201 and out of the sensor 200. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas (or intake air). A control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that the oxygen sensor described herein is merely an example embodiment of an oxygen sensor, and that other embodiments of oxygen sensors may have additional and/or alternative features and/or designs.

In this way, the oxygen sensor of FIG. 2 may be a variable voltage oxygen sensor configured to operate at a first, lower voltage where water molecules are not dissociated and a second, higher voltage where water molecules are fully dissociated. As such the second voltage is higher than the first voltage. However, as described above, continuously operating the oxygen sensor in the variable voltage (VVs mode), and particularly at the higher second voltage, may degrade the oxygen sensor, thereby reducing the longevity of the sensor. Thus, it may be advantageous to reduce the amount of time the oxygen sensor spends operating at the higher, second voltage. As a result, sensor degradation may be reduced, thereby increasing the longevity of the sensor and producing more accurate sensor outputs for engine control.

As elaborated below, the oxygen sensor of FIG. 2 can be advantageously used to estimate an ambient humidity which may subsequently be used to adjust engine operating such as adjusting EGR flow, air-fuel ratio, spark timing, etc. In particular, an estimated dry air oxygen reading may be determined based on a ratio between an oxygen sensor output at a first, lower voltage and an oxygen sensor output at a second, higher voltage. During engine operation at selected conditions, a third oxygen sensor output at the first, lower voltage may be determined and then compared to the dry air oxygen reading to determine ambient humidity. Multiple oxygen sensor readings at the first, lower voltage may be taken to determine consecutive and updated ambient humidity estimates based on a same (e.g., previously determined) dry air oxygen reading. In this way, the oxygen sensor may spend an increased amount of time operating at the first, lower voltage and not in VVs mode, thereby reducing degradation of the sensor.

Continuing to FIG. 3, a flow chart illustrating a routine 300 for determining a dry air oxygen reading with an oxygen sensor, such as the oxygen sensor 200 described above with reference to FIG. 2, is shown. Specifically, the routine 300 determines a dry air oxygen reading based on different voltages (e.g., reference voltages) applied to a pumping cell of the oxygen sensor during selected engine operating conditions. The resulting dry air oxygen reading may then be used along with subsequent oxygen sensor outputs during additional select operating conditions to estimate ambient humidity, as described further below with reference to FIG. 5.

At 310 of routine 300, engine operating conditions are determined. Engine operating conditions may include but are not limited to air-fuel ratio, amount of EGR entering the combustion chambers, and fueling conditions, for example.

Once the engine operating conditions are determined, routine 300 continues to 312 where it is determined if selected conditions are met. For example, when the oxygen sensor is an intake oxygen sensor positioned in the intake passage (or an intake manifold), the selected conditions may include EGR being enabled and no purge or crankcase ventilation gases being received in the intake manifold. Alternatively, the selected conditions may include no purge or crankcase ventilation gases being received upstream of the intake oxygen sensor. As another example, when the oxygen sensor is an exhaust gas oxygen sensor positioned in the exhaust passage, the selected conditions may include engine non-fueling conditions. Non-fueling conditions include vehicle deceleration conditions and engine operating conditions in which the fuel supply is interrupted but the engine continues spinning and at least one intake valve and one exhaust valve are operating; thus, air is flowing through one or more of the cylinders, but fuel is not injected in the cylinders. Under non-fueling conditions, combustion is not carried out and ambient air may move through the cylinder from the intake to the exhaust. In this way, a sensor, such as an intake or exhaust oxygen sensor, may receive ambient air on which measurements, such as ambient humidity detection, may be performed.

As noted, non-fueling conditions may include, for example, deceleration fuel shut-off (DFSO). DFSO is responsive to the operator pedal (e.g., in response to a driver tip-out and where the vehicle accelerates greater than a threshold amount). DSFO conditions may occur repeatedly during a drive cycle, and, thus, numerous indications of the ambient humidity may be generated throughout the drive cycle, such as during each DFSO event. As such, the fuel type may be identified accurately based on an amount of water in the exhaust gas despite fluctuations in humidity between drive cycles or even during the same drive cycle.

Further, the selected conditions at 312 may additionally include following an engine start or a duration of engine operation (e.g., a number of travel miles, an amount of time, or a number of engine cycles). For example, if the oxygen sensor is an intake oxygen sensor, the selected conditions at 312 may include following an engine start (or after a duration of engine operation) when purge and positive crankcase ventilation (PCV) flow to the intake manifold is disabled. In another example, if the oxygen sensor is an exhaust gas sensor, the selected conditions at 312 may include following an engine start (or after a duration of engine operation) during engine non-fueling conditions (e.g., when fueling is disabled as described above). In this way, learning the dry air oxygen reading as described further below may only occur periodically after each engine start or after a duration of engine operation when a flow of hydrocarbons past the oxygen sensor are reduced. In this way, a more accurate sensor reading may be obtained while reducing an amount of time of operating the oxygen sensor in VVs mode.

Continuing with FIG. 3, if it is determined that the selected operating conditions are not met, the routine 300 continues to 313 to continue current oxygen sensor operation (at the current pumping voltage, such as at the base or lower, first reference voltage) and determine ambient humidity based on a previously determined dry air pumping current (e.g., dry air oxygen reading). As such, the method at FIG. 5 may include determining ambient humidity using a previously stored dry air oxygen reading from a previous dry air oxygen reading learning routine. For example, following each execution of routine 300 where a dry air oxygen reading is determined, the resulting dry air oxygen reading (e.g., pumping current) value may be stored in a memory of the controller. Then, during the routine of FIG. 5, the most recently stored dry air pumping current may be looked up in the memory of the controller and used to determine ambient humidity. The method at 313 may include not operating the oxygen sensor in the VVs mode and instead continuing to operate the oxygen sensor at the lower, first reference voltage, also referred to herein as the base reference voltage. Operating the oxygen sensor at the base reference voltage may result in less sensor degradation than when operating the oxygen sensor at the higher, second reference voltage.

Conversely at 312, if is determined that selected operating conditions are met, routine 300 continues to 314 where a first pumping voltage ($V_1$) (e.g., first reference voltage) is applied to the oxygen pumping cell of the oxygen sensor and a first pumping current ($I_{p1}$) is received. The first pumping voltage may have a value such that oxygen is pumped from the cell, but low enough that oxygen compounds such as $H_2O$ (e.g., water) are not dissociated (e.g., $V_1$=450 mV). For example, at the first pumping voltage, the oxygen sensor may not dissociate any water molecules. Application of the first voltage generates an output of the sensor in the form of the first pumping current ($I_{p1}$) that is indicative of the amount of oxygen in the sample gas. In this example, because the engine is under selected conditions (such as non-fueling conditions), the amount of oxygen may correspond to the amount of oxygen in the fresh air surrounding the vehicle, or a humid air oxygen reading.

Once the amount of oxygen is determined, routine 300 proceeds to 316 where a second pumping voltage ($V_2$) (e.g., reference voltage) is applied to the oxygen pumping cell of the oxygen sensor and a second pumping ($I_{p2}$) current is received. The second voltage may be greater than the first voltage applied to the sensor. In particular, the second voltage may have a value high enough to dissociate a desired oxygen compound. For example, the second voltage may be high enough to dissociate all $H_2O$ molecules into hydrogen and oxygen (e.g., $V_2$=1.1 V). Application of the second voltage generates the second pumping current ($I_2$) that is indicative of the amount of oxygen and water in the sample gas. It will be understood that the term "water" in the "amount of oxygen and water" as used herein refers to the amount of oxygen from the dissociated $H_2O$ molecules in the sample gas.

In one particular example, the second voltage (e.g., second reference voltage) may be 1080 mV, at which the water in the air is fully (e.g., completely) dissociated (e.g., 100% of the water in the air is dissociated at 1080 mV). This second voltage may be larger than a third, middle voltage where water in the air is partially dissociated (e.g., approximately 40% of the water in the air is dissociated). In one example, the third, middle voltage may be about 920 mV. In another example, the third, middle voltage may be about 950 mV. As an example, a graph 400 of FIG. 4 shows oxygen sensor output over a range of humidity conditions (e.g., from 1.5% humidity to 4% humidity). As shown, the sensor output at 920 mV corresponds to a dry air reading under the range of humidity conditions. The sensor output at 1.1 V corresponds to a humid air reading where all the water in the air has been dissociated at the sensor and the sensor output at 4.5 V corresponds to a humid air reading where no water in the air has been dissociated. Thus, a dry air oxygen reading may be obtained by a ratio of oxygen sensor outputs when the oxygen sensor is operated at 4.5 V and 1.1V. In an alternate embodiment, the dry air oxygen reading may be obtained by a ratio of oxygen sensor output when the oxygen sensor is operated at a voltage below 0.92 V where water is not dissociated (e.g., not even partially dissociated) and a voltage above 0.92 V where water is fully dissociated (e.g., 100% dissociated).

At 318, the dry air oxygen reading and related correction factor are determined based on the first pumping current and the second pumping current. For example, as described above, by operating the sensor at 450 mV (or a similar voltage where no water is dissociated at the sensor), a lower pumping current and oxygen reading may be obtained and by operating the sensor at 1080 mV (or a similar voltage where all water is dissociated at the sensor) a higher pumping current and oxygen reading may be obtained. A dry air pumping current indicative of a dry air oxygen reading may then be estimated from a ratio between the lower, first pumping current and the higher, second pumping current. For example, a sum of 40% of the higher, second pumping current and 60% of the lower, first pumping current may be substantially equal to the dry air pumping current and oxygen reading. In an alternate example, different percentages of the higher and lower pumping current may be added together to determine the dry air pumping current. For example, if the higher or lower voltage differ from 450 mV and 1080 mV, respectively, the corresponding percentages used to determine the ratio between the higher and lower pumping currents may differ proportionally.

The estimated dry air oxygen reading based on the ratio between the higher and lower pumping currents (e.g., higher and lower oxygen sensor outputs corresponding to the higher and lower voltages) may then be used to determine an ambient humidity estimate at 320, as described further below with reference to FIG. 5. For example, the method at 320 may include storing the determined dry air oxygen reading (e.g., as a dry air pumping current value) in a memory of the controller. Then, during the routine of FIG. 5, the controller may look-up the most recently stored dry air oxygen reading and comparing it to another oxygen sensor output under select engine operating conditions to determine the ambient humidity estimate. Further, the method at 320 may include updating a previously stored dry air oxygen reading with a new dry air oxygen reading in the memory of the controller. For example, the stored dry air oxygen reading may be updated following each engine start.

Figure 5:
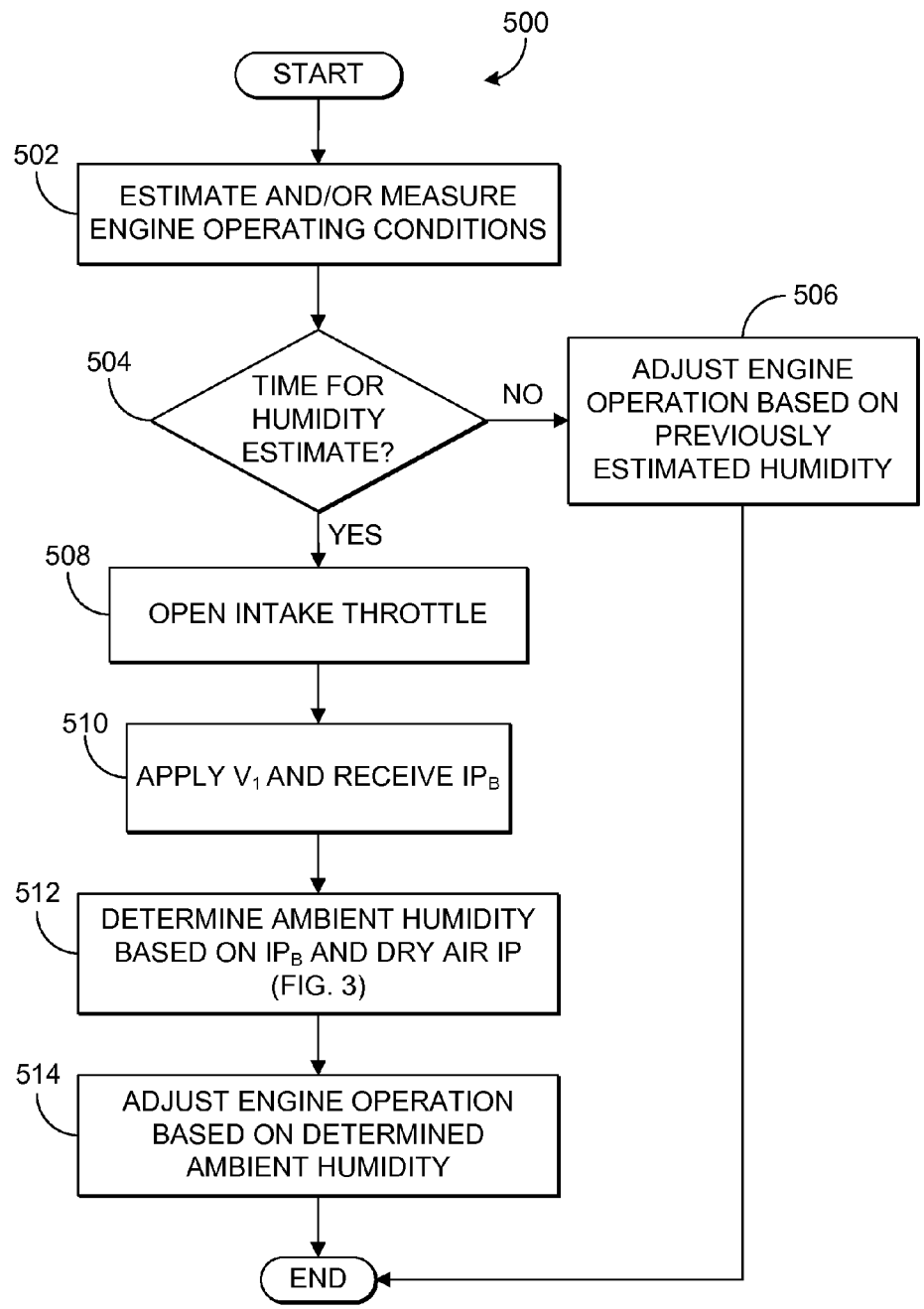
FIG. 5 shows a flow chart illustrating a routine for estimating ambient humidity based a dry air pumping current reading and an output of an intake or exhaust gas oxygen sensor.

Referring now to FIG. 5, a flow chart depicting a control routine 500 for adjusting engine operation based on ambient humidity estimated based on the dry air oxygen reading and an additional output of the oxygen sensor during select engine operating conditions is shown. Instructions for carrying out routine 500 (and routine 300 described above) may be stored on a memory of a controller (such as controller 12 shown in FIG. 1). Further, the controller may execute routine 500 as described further below.

Routine 500 begins at 502 by estimating and/or measuring engine operating conditions. Engine operating conditions may include engine speed and load, EGR flow, air-fuel ratio, mass air flow, MAP, etc. At 504, the routine includes determining if it is time for an ambient humidity estimate. Determining if it is time for an ambient humidity estimate may include determining if select engine operating conditions are met. In one example, if the oxygen sensor is an intake oxygen sensor positioned in an intake passage and/or intake manifold upstream of the engine, the select engine operating conditions may include when fuel canister purge and crankcase gases are not flowing to the intake manifold.

In another example, if the oxygen sensor is an exhaust oxygen sensor positioned in an exhaust passaged downstream from the engine (e.g., downstream of an engine cylinder exhaust valve), the select engine operating conditions may include during engine non-fueling conditions, as described above with reference to FIG. 3. For example, the engine non-fueling conditions may include when no fuel is being injected into the engine cylinder while at least one intake valve and one exhaust valve are still operating. In another example, the engine non-fueling conditions may include a DFSO event. In this way, the select engine operating conditions may include conditions in which an amount of hydrocarbons flowing past the oxygen sensor is reduced.

At 508 the routine includes opening an intake throttle (e.g., throttle 62 shown in FIG. 1) to further reduce the amount of hydrocarbons flowing past the oxygen sensor. If the oxygen sensor is an exhaust oxygen sensor, opening the throttle may reduce the amount of hydrocarbons from PCV coming through the exhaust air. For example, if the intake throttle is closed during the engine non-fueling condition, a large intake manifold vacuum is generated which can draw in positive crankcase ventilation (PCV) hydrocarbons. As such, even if a PCV port is closed during the DFSO, the vacuum may be sufficiently strong to draw in PCV hydrocarbons through the piston rings. The PCV flow drawn in may be aggravated in an aging engine due to leakage of PCV gases past the piston rings and valves. The ingested hydrocarbons may affect the output of the exhaust gas sensor and can confound the humidity measurements. In particular, the hydrocarbon effect leads to a sensor output that overestimates the ambient humidity. Thus, when the oxygen sensor is an exhaust oxygen sensor, routine 500 includes opening the intake throttle at 508 before determining the oxygen sensor output.

At 510 the routine includes applying the first, lower reference voltage (e.g., base voltage, $V_1$) to the oxygen sensor and a pumping current ($Ip_B$) is received. As such, the method at 510 includes not operating the oxygen sensor in VVs mode and instead maintaining the reference voltage of the sensor at a lower, based level that reduced oxygen sensor degradation. Said another way, the method at 510 includes not modulating the reference voltage of the oxygen sensor between a lower first voltage and a higher second voltage. The resulting pumping current may be indicative of the amount of oxygen in the sample gas.

The routine then continues on to 512 to determine ambient humidity based on $Ip_B$ (the pumping current determined at 510 during non-VVs sensor operation) and the dry air pumping current determined during routine 300. As explained above, the controller may look up the most recently stored value of the dry air pumping current to use at 512. The amount of oxygen reduction due to the dilution effect of ambient humidity may then be determined based on the difference between the dry air pumping current and the pumping current $Ip_B$ determined at 510. By multiplying by a conversion factor, this difference may then be converted from a pumping current to a humidity percentage. In this way, by comparing the output of the oxygen sensor operating in non-VVs mode at the base reference voltage to a stored dry air pumping current value, ambient humidity may be determined with continuously operating the oxygen sensor in VVs mode.

Once the ambient humidity is determined, the routine continues to 514 where one or more operating parameters are adjusted based on the determined ambient humidity. Such operating parameters may include an amount of EGR, spark timing, and air-fuel ratio, among others. As described above, in internal combustion engines, it is desirable to schedule engine operating parameters, such as spark timing, in order to optimize engine performance. In some embodiments, only one parameter may be adjusted responsive to the humidity. In other embodiments, any combination or sub-combination of these operating parameters may be adjusted in response to measured fluctuations in ambient humidity.

In one example embodiment, an amount of EGR may be adjusted based on the measured ambient humidity. For example, in one condition, the water concentration in the air surrounding the vehicle may have increased due to a weather condition such as fog; thus, a higher humidity is detected by the exhaust gas sensor during engine non-fueling conditions. In response to the increased humidity measurement, during subsequent engine fueling operation, the EGR flow into at least one combustion chamber may be reduced. As a result, engine efficiency may be maintained.

Responsive to a fluctuation in absolute ambient humidity, EGR flow may be increased or decreased in at least one combustion chamber. As such, the EGR flow may be increased or decreased in only one combustion chamber, in some combustion chambers, or in all combustion chambers. Furthermore, the magnitude of change of the EGR flow may be the same for all cylinders or the magnitude of change of the EGR flow may vary by cylinder based on the specific operating conditions of each cylinder.

In another embodiment, spark timing may be adjusted responsive to the ambient humidity. In at least one condition, for example, spark timing may be advanced in one or more cylinders during subsequent engine fueling operation responsive to a higher humidity reading. Spark timing may be scheduled so as to reduce knock in low humidity conditions (e.g., retarded from a peak torque timing), for example. When an increase in humidity is detected by the exhaust gas sensor, spark timing may be advanced in order to maintain engine performance and operate closer to or at a peak torque spark timing.

Additionally, spark timing may be retarded in response to a decrease in ambient humidity. For example, a decrease in ambient humidity from a higher humidity may cause knock. If the decrease in humidity is detected by the exhaust gas sensor during non-fueling conditions, such as DFSO, spark timing may be retarded during subsequent engine fueling operation and knock may be reduced.

It should be noted that spark may be advanced or retarded in one or more cylinders during subsequent engine fueling operation. Further, the magnitude of change of spark timing may be the same for all cylinders or one or more cylinders may have varying magnitudes of spark advance or retard.

In still another example embodiment, exhaust gas air fuel ratio may be adjusted responsive to the measured ambient humidity during subsequent engine fueling operation. For example, an engine may be operating with a lean air fuel ratio optimized for low humidity. In the event of an increase in humidity, the mixture may become diluted, resulting in engine misfire. If the increase in humidity is detected by the exhaust gas sensor during non-fueling conditions, however, the air fuel ration may be adjusted so that the engine will operate with a less lean, lean air fuel ratio during subsequent fueling operation. Likewise, an air fuel ratio may be adjusted to be a more lean, lean air fuel ratio during subsequent engine fueling operation in response to a measured decrease in ambient humidity. In this way, conditions such as engine misfire due to humidity fluctuations may be reduced.

In some examples, an engine may be operating with a stoichiometric air fuel ratio or a rich air fuel ratio. As such, the air fuel ratio may be independent of ambient humidity and measured fluctuations in humidity may not result in an adjustment of air fuel ratio.

In this way, engine operating parameters may be adjusted responsive to an ambient humidity generated by an oxygen sensor coupled to an engine (either in an intake or an exhaust system). As DFSO or disabled purge and PCV flow may occur numerous times during a drive cycle, an ambient humidity measurement may be generated several times throughout the drive cycle and one or more engine operating parameters may be adjusted accordingly, resulting in an optimized overall engine performance despite fluctuations in ambient humidity. Furthermore, the indication of ambient humidity may be determined without continuously operating the oxygen sensor in VVs mode (e.g., modulating between the lower first reference voltage and the higher second reference voltage). Instead, one dry air oxygen reading may be determined at each engine start or after a duration of engine use. This one dry air oxygen reading may then be compared to each oxygen sensor output during the selected conditions for ambient humidity determination without having to operate the oxygen sensor at the higher reference voltage. In this way, a technical effect of the invention is achieved by reducing a duration of operating the oxygen sensor in VVs mode, thereby reducing degradation and increasing longevity of the oxygen sensor. At the same time, ambient humidity measurements of increased accuracy may be obtained for increased engine control.

As one embodiment, a method comprises applying to an oxygen sensor a lower first reference voltage to generate a first output and a higher second reference voltage to generate a second output during a first condition; applying the first reference voltage to the oxygen sensor to generate a third output during a second condition; and adjusting engine operation based on ambient humidity estimated based on the first, second, and third output. The method may further comprise, during the second condition, opening an intake throttle and then generating the third output from the oxygen sensor. Additionally, the second condition may occur more frequently than the first condition. Further, applying the first reference voltage to the oxygen sensor to generate the third output may include applying only the first reference voltage to the oxygen sensor and not applying the second reference voltage to the oxygen sensor. As such, during generating the third output, the reference voltage of the oxygen sensor may be maintained at the lower, first reference voltage and not increased to the second voltage.

In one example, the oxygen sensor is a universal exhaust gas oxygen sensor coupled to an exhaust manifold of an engine, upstream of an exhaust catalyst, and the second condition includes engine non-fueling conditions where at least one intake valve and one exhaust valve are operating. For example, the engine non-fueling conditions may include a deceleration fuel shut-off event. In another example, the oxygen sensor is an intake oxygen sensor coupled to an intake manifold of an engine, upstream of an intake compressor and the second condition includes when no fuel canister purge gases or crankcase gases are being received in the intake manifold. Thus, the second condition may include when boost is off and a fuel canister purge valve is closed.

The first condition may include an engine non-fueling condition when the oxygen sensor is an exhaust oxygen sensor or no purge and crankcase gas flow to an intake manifold when the oxygen sensor is an intake oxygen sensor following one or more of an engine start and a duration of engine operation. Said another way, the first condition may only occur following one or more of an engine start and a duration of engine operation when the conditions of the second condition are met. Additionally, the first output includes a first pumping current generated responsive to applying the first reference voltage, the second output includes a second pumping current generated responsive to applying the second reference voltage, where the first output is indicative of a humid air oxygen reading and the second output is indicative of an increase in oxygen due to dissociation of humid air. Further still, a dry air pumping current is based on a ratio between the first output and the second output, the dry air pumping current indicative of a dry air oxygen reading. In one example, the first reference voltage is a reference voltage where water molecules are not dissociated and the second reference voltage is a reference voltage where water molecules are fully dissociated. As one example, adjusting engine operation includes adjusting an amount of exhaust gas recirculation, and, in at least one condition, adjusting the amount of exhaust gas recirculation includes reducing the amount of exhaust gas recirculation responsive to an indication of higher humidity. As another example, adjusting engine operation includes adjusting an engine combustion air fuel ratio, and adjusting the engine combustion air fuel ratio includes maintaining a desired exhaust air fuel ratio based on the oxygen sensor.

As another embodiment, a method for an engine comprises: after a duration of engine operation and during a first condition, operating an oxygen sensor at a lower reference voltage where water molecules are not dissociated to generate a first output and at a higher reference voltage where water molecules are fully dissociated to generate a second output; during subsequent operation at the first condition, opening an intake throttle and operating the oxygen sensor at the lower reference voltage to generate a third output; and estimating an ambient humidity based on the first, second, and third output. In one example, the oxygen sensor is an exhaust oxygen sensor positioned in an exhaust passage of the engine and the first condition includes engine non-fueling conditions where at least one intake valve and one exhaust valve are operating. For example, the exhaust oxygen sensor may be located upstream of an exhaust catalyst and upstream of an inlet of an exhaust gas recirculation passage configured to recirculate exhaust residuals from an exhaust manifold to an intake manifold of the engine. In another example, the oxygen sensor is an intake oxygen sensor positioned in an intake manifold of the engine and the first condition includes when no purge or crankcase gases are flowing to the intake manifold upstream of the intake oxygen sensor.

Additionally, the first output includes a first pumping current generated responsive to operating at the lower reference voltage and the second output includes a second pumping current generated responsive to operating at the higher reference voltage, the first and second outputs indicative of a humid air oxygen amount, and the lower reference voltage is below a middle reference voltage and the higher reference voltage is above the middle reference voltage, the middle reference voltage generating a third pumping current indicative of a dry air oxygen amount.

The method may further comprise adjusting one or more engine operating parameters based on the estimated ambient humidity, where the one or more engine operating parameters include an amount of exhaust gas recirculation, spark timing, and engine air fuel ratio. Further, after the duration of engine operation may include one or more of after each engine start, after a number of engine cycles, after a period of engine use, and after a vehicle in which the engine is installed travels a threshold distance.

As yet another embodiment, a system comprises an engine with an exhaust system, an exhaust oxygen sensor disposed in the exhaust system, and a controller in communication with the exhaust oxygen sensor, the controller including computer readable instructions for: periodically determining a dry air pumping current based on a first output of the exhaust oxygen sensor upon applying a lower first reference voltage at which water molecules are not dissociated and a second output of the exhaust oxygen sensor upon applying a higher second reference voltage at which water molecules are fully dissociated; during engine non-fueling conditions where at least one intake valve and one exhaust valve are operating, operating the exhaust oxygen sensor at only the lower first reference voltage to generate a third output; and estimating ambient humidity based on the first output, the second output, and a third output. The system may further comprise an intake throttle and wherein the computer readable instructions further include instructions for opening the intake throttle before operating the exhaust oxygen sensor to generate the third output.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
    applying to an oxygen sensor a lower first reference voltage to generate a first output of the oxygen sensor and a higher second reference voltage to generate a second output of the oxygen sensor during a first condition;
    applying only the first reference voltage to the oxygen sensor during a second condition and generating a third output of the oxygen sensor during applying only the first reference voltage; and
    adjusting engine operation based on ambient humidity estimated based on the first, second, and third outputs.

2. The method of claim 1, further comprising, during the second condition, in response to an intake throttle being closed, opening the intake throttle and then generating the third output from the oxygen sensor and wherein the second condition occurs more frequently than the first condition.

3. The method of claim 1, wherein the oxygen sensor is a universal exhaust gas oxygen sensor coupled to an exhaust manifold of an engine, upstream of an exhaust catalyst, and wherein the second condition includes engine non-fueling conditions where at least one intake valve and one exhaust valve are operating.

4. The method of claim 3, wherein the engine non-fueling conditions include a deceleration fuel shut-off event.

5. The method of claim 1, wherein the oxygen sensor is an intake oxygen sensor coupled to an intake manifold of an engine, upstream of an intake compressor.

6. The method of claim 5, wherein the second condition includes when no fuel canister purge gases or crankcase gases are being received in the intake manifold.

7. The method of claim 1, wherein the first condition includes an engine non-fueling condition when the oxygen sensor is an exhaust oxygen sensor or no purge and crankcase gas flow to an intake manifold when the oxygen sensor is an intake oxygen sensor following one or more of an engine start and a duration of engine operation.

8. The method of claim 1, wherein the first output includes a first pumping current generated responsive to applying the first reference voltage, wherein the second output includes a second pumping current generated responsive to applying the second reference voltage, wherein the first output is indicative of a humid air oxygen reading and the second output is indicative of an increase in oxygen due to dissociation of humid air, and wherein a dry air pumping current is based on a ratio between the first output and the second output, the dry air pumping current indicative of a dry air oxygen reading.

9. The method of claim 1, wherein the first reference voltage is a reference voltage where water molecules are not dissociated and the second reference voltage is a reference voltage where water molecules are fully dissociated, and wherein applying only the first reference voltage to the oxygen sensor during the second condition and generating the third output of the oxygen sensor during applying only the first reference voltage includes not applying the second reference voltage to the oxygen sensor during the second condition.

10. The method of claim 1, wherein adjusting engine operation includes adjusting an amount of exhaust gas recirculation, and, in at least one condition, adjusting the amount of exhaust gas recirculation includes reducing the amount of exhaust gas recirculation responsive to an indication of higher humidity.

11. The method of claim 1, wherein adjusting engine operation includes adjusting an engine combustion air fuel ratio, and adjusting the engine combustion air fuel ratio includes maintaining a desired exhaust air fuel ratio based on the oxygen sensor.

12. A method for an engine, comprising:
after a duration of engine operation and during a first condition, operating an oxygen sensor at a lower reference voltage where water molecules are not dissociated to generate a first output and at a higher reference voltage where water molecules are fully dissociated to generate a second output;
during subsequent operation at the first condition, opening an intake throttle and operating the oxygen sensor at the lower reference voltage to generate a third output; and
estimating an ambient humidity based on the first, second, and third outputs, wherein the oxygen sensor is an intake oxygen sensor positioned in an intake manifold of the engine and wherein the first condition includes when no purge or crankcase gases are flowing to the intake manifold upstream of the intake oxygen sensor.

13. The method of claim 12, wherein the first output includes a first pumping current generated responsive to operating at the lower reference voltage and the second output includes a second pumping current generated responsive to operating at the higher reference voltage, the first and second outputs indicative of a humid air oxygen amount, and wherein the lower reference voltage is below a middle reference voltage and the higher reference voltage is above the middle reference voltage, the middle reference voltage generating a third pumping current indicative of a dry air oxygen amount.

14. The method of claim 12, further comprising adjusting one or more engine operating parameters based on the estimated ambient humidity, where the one or more engine operating parameters include an amount of exhaust gas recirculation, spark timing, and engine air fuel ratio.

15. The method of claim 14, wherein after the duration of engine operation includes one or more of after each engine start, after a number of engine cycles, after a period of engine use, and after a vehicle in which the engine is installed travels a threshold distance.

16. A system, comprising:
an engine with an exhaust system;
an exhaust oxygen sensor disposed in the exhaust system; and
a controller in communication with the exhaust oxygen sensor, the controller including computer readable instructions for:
periodically determining a dry air pumping current based on a first output of the exhaust oxygen sensor upon applying a lower first reference voltage at which water molecules are not dissociated and a second output of the exhaust oxygen sensor upon applying a higher second reference voltage at which water molecules are fully dissociated;
during engine non-fueling conditions where at least one intake valve and one exhaust valve are operating, operating the exhaust oxygen sensor at only the lower first reference voltage and generating a third output during operating the exhaust oxygen sensor at only the lower first reference voltage; and
estimating ambient humidity based on the first output, the second output, and the third output.

17. The system of claim 16, further comprising an intake throttle and wherein the computer readable instructions further include instructions for opening the intake throttle before generating the third output.

18. The method of claim 1, wherein applying only the first reference voltage to the oxygen sensor during the second condition and generating the third output of the oxygen sensor during applying only the first reference voltage includes maintaining a reference voltage of the oxygen sensor at the first deference voltage via applying only the first reference voltage to the oxygen sensor and not applying the second reference voltage to the oxygen sensor during the second condition.

19. The method of claim 1, further comprising determining the estimated ambient humidity based on only the first, second, and third outputs.

* * * * *